United States Patent [19]

Massonneau et al.

[11] Patent Number: 4,925,950
[45] Date of Patent: May 15, 1990

[54] PROCESS FOR PREPARING 1-HYDROXYALKYL-5-NITROIMIDAZOLE

[75] Inventors: Viviane Massonneau; Michel Mulhauser, both of Ecully; Albert Buforn, Lyons, all of France

[73] Assignee: Rhone-Poulenc Sante, Antony, France

[21] Appl. No.: 296,688

[22] Filed: Jan. 13, 1989

[30] Foreign Application Priority Data

Jan. 15, 1988 [FR] France .................. 88 00416

[51] Int. Cl.⁵ .................. C07D 233/94; C07D 405/06
[52] U.S. Cl. .................. 548/338; 548/336; 548/339; 548/340
[58] Field of Search .................. 548/338, 336, 339, 340

[56] References Cited

PUBLICATIONS

Fieser, L. et al., *Reagents for Organic Synthesis*, John Wiley, New York, 1967, pp. 294–295.
*Chemical Abstracts*, 77:139490t (1972), [D. Tomalia et al., *J. Heterocycl. Chem.*, 1972, 9(4), 891–4].

*Primary Examiner*—Richard A. Schwartz
*Attorney, Agent, or Firm*—Stevens, Davis, Miller & Mosher

[57] ABSTRACT

Hydroxyalkylating agents of formula:

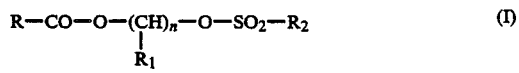

in which R denotes alkyl, n is 2 or 3, $R_1$ denotes hydrogen or alkyl and $R_2$ denotes alkyl an unsubstituted or substituted phenyl or

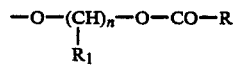

are useful inter alia for the preparation of 1-(hydroxyalkyl)imidazoles. They are made by reaction of a sulphonic acid or dimethyl sulphate with a corresponding decarboxylate ester.

8 Claims, No Drawings

PROCESS FOR PREPARING 1-HYDROXYALKYL-5-NITROIMIDAZOLE

The present invention relates to the preparation of hydroxyalkylating agents, to agents so obtained and to their use.

The invention provides a process for the preparation of hydroxyalkylating agents of formula:

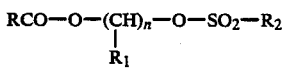

in which R denotes alkyl of 1 to 4 carbon atoms, n is 2 or 3, the symbols $R_1$, which may be identical or different, denote hydrogen or alkyl of 1 to 4 carbon atoms, and $R_2$ denotes alkyl of 1 to 4 carbon atoms, unsubstituted or substituted phenyl or

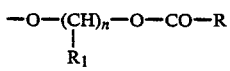

in which R, n and $R_1$ are defined as above so that in the two radicals

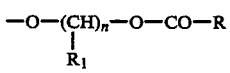

the symbols R, n and $R_1$ have the same meanings

More especially, the invention relates to the preparation of the products of formula (I) in which: R denotes methyl n is 2 one of the symbols $R_1$ denotes hydrogen and the other denotes hydrogen or methyl, and $R_2$ denotes methyl or

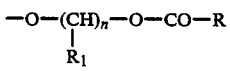

in which R denotes methyl, n is 2 and one of the symbols $R_1$ denotes hydrogen and the other denotes hydrogen or methyl More particularly, the invention relates to the preparation of di(2-acetoxyethyl) sulphate and 2-acetoxyethyl mesylate According to a feature of the present invention, the products of the formula (I) are obtained by reacting an acid of formula:

                                 (II)

in which $R_3$ denotes hydroxy, alkyl of 1 to 4 carbon atoms, or an unsubstituted or substituted phenyl, with a diester of formula:

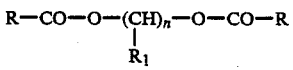                                 (III)

which may be in excess, and in which R, n and $R_1$ are defined as above, at a temperature of from 80° to 160° C. and removing the acid formed (RCOOH) by distillation under reduced pressure as it forms and, where appropriate, the excess diester.

The products of formula (I) in which $R_2$ denotes

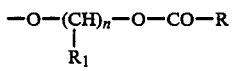

may also be obtained by the action of methyl sulphate on an ester of formula III, which may be an excess, at a temperature from 80° to 160° C. and removing the methyl ester formed ($RCOOCH_3$) by distillation under reduced pressure and, where appropriate, the excess diester.

All these reactions are performed by heating under reduced pressure (preferably 10 to 200 mm Hg; 1.3 to 26.6 kPa) at a temperature of from 80° to 160° C., and removing the acid formed (RCOOH) or its methyl ester by distillation, as well as, where appropriate, the excess ester of general formula (III).

In general, the product of formula (I) thereby obtained can be used without subsequent purification.

The present invention also provides the products of formula (I) in which $R_2$ denotes

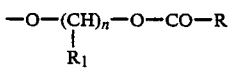

in which n, R and $R_1$ are defined as above, and more especially to di(2-acetoxyethyl) sulphate, which are new compounds.

The products of formula (I) are especially useful for carrying out hydroxylation reactions. For example, they may be used for preparing 1-(hydroxyalkyl)nitroimidazoles which possess noteworthy therapeutic properties, such as 1-hydroxyethyl-2-methyl-5-nitroimidazole (metronidazole) or 1-(2-hydroxypropyl)-2-methyl-5-nitroimidazole (secnidazole) or 1-(3-hydroxypropyl)-2-methyl-5-nitroimidazole (ternidazole).

According to a further feature of the present invention, 1-(hydroxyalkyl)nitroimidazole are obtained by a process which comprises condensing a product of formula (I) at 60° C. to 100° C. with an imidazole derivative of formula:

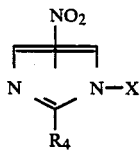                                 (IV)

in which $R_4$ denotes hydrogen, alkyl of 1 to 4 carbon atoms, or alkenyl of 2 to 4 carbon atoms, the said alkyl and alkenyl radicals being unsubstituted or substituted by one or more identical or different radicals chosen from phenyl, phenoxy, and 5- or 6-membered oxygen-containing heterocyclic radicals:

or alternatively $R_4$ denotes an aryl of 6 to 10 carbon atoms, unsubstituted or substituted by one or more identical or different substituents chosen from halogen, alkyl of 1 to 4 carbon atoms, alkoxy of 1 to 4 carbon atoms, phenyl, phenoxy and nitro, or alternatively $R_4$ denotes a cycloalkyl of 5 or 6 carbon atoms; the aforesaid phenyl, phenoxy and heterocyclic radicals being unsubstituted or substituted by one or more identical or different substituents chosen from halogen, alkyl of 1 to 4 carbon atoms, alkoxy of 1 to 4 carbon atoms, phenyl, phenoxy and nitro; and X denotes hydrogen, or a hydroxymethyl radical, an alkoxymethyl radical in which the alkyl portion contains 1 to 4 carbon atoms, an acyloxymethyl radical in which the acyl portion contains 1 to 4 carbon atoms, an allylic ethylene radical such as allyl, or an arylmethyl radical such as benzyl; hydrolysing or alcoholysing the product and isolating the 1-(hydroxyalkyl)imidazole.

The condensation is performed at a temperature from 60° to 100° C., preferably in the region of 80° C., and optionally in an organic solvent chosen from esters (eg.methylacetate, ethyl acetate), ethers (methyl tert-butyl ether), ketones (methyl isobutyl ketone) or aromatic hydrocarbons (toluene, xylene).

In general, the hydrolysis or alcoholysis is performed by heating in water or an alcohol (methanol, ethanol) at a temperature from 60° to 100° C.

The 1-hydroxyalkyl-5-nitroimidazole thereby obtained is isolated from the reaction mixture according to the usual methods, at a pH in the region of 10.

The imidazole derivative of formula (IV) may be prepared under the conditions described in British Pat. GB 1,026,631.

The examples which follow illustrate the present invention.

EXAMPLE 1

A. Glycol diacetate (292.3 g; 2 moles) and dimethyl sulphate (50.4 g; 0.4 mole) are introduced into a distillation apparatus in which the receiver is immersed in an acetone/dry ice bath. A pressure of 200 mm Hg (26.6 kPa) is established in the apparatus, and the reaction mixture is then heated for 5 hours to 150° C. During the heating, methyl acetate (60 cc) is distilled off. The reaction mixture is cooled to approximately 100° C. and glycol diacetate (206 cc) is then distilled off under a pressure of 1 mm Hg (0.13 kPa) (bath temperature: 110° C; vapour temperature: 65° C).

In the boiling vessel, di(2-acetoxyethyl) sulphate is recovered in the form of a pale yellow oil.

The di(2-acetoxyethyl) sulphate is characterized by:
its infrared spectrum, in which the main characteristic absorption bands expressed in $cm^{-1}$ are 1740 (acetate C=O); 1395-1195 (C—O—$SO_2$—O—C) and 1245 (C-0)

its proton nuclear magnetic resonance spectrum (360 MHz; $CD_3CN$; chemical shifts in ppm): 4.45 (t); 4.31 (t) and 2 (s).

B. Di(2-acetoxyethyl) sulphate (2.7 g; 0.01 mole) and 1-acetoxymethyl-2-methyl-4-nitroimidazole (1.99 g; 0.01 mole) are introduced into a round-bottomed flask equipped with a magnetic stirrer. The reaction mixture is heated to 80° C. for 5 hours. Water (5 cc) is then added and heating is continued at 80° C. for 3 hours.

After the mixture is cooled, metronidazole (1.10 g) and 2-methyl-4(or 5)-nitroi idazole (0.288 g) are assayed by high performance liquid chromatography (HPLC).

The degree of conversion of 1-acetoxymethyl-2-methyl-4-nitroimidazole is 77.3%.

The yield of metronidazole is 64.2% relative to the 1-acetoxymethyl-2-methyl-4-nitroimidazole introduced and 83% relative to the 1-acetoxymethyl-2-methyl-4-nitroimidazole converted.

EXAMPLE 2

Di(2-acetoxyethyl) sulphate (10.8 g; 0.04 mole), prepared under the conditions of Example 1, and 1-acetoxymethyl-2-methyl-4-nitroimidazole (7.96 g; 0.04 mole) are introduced into a round-bottomed flask equipped with a magnetic stirrer. The reaction mixture is heated to 80° C. for 4 hours. Methanol (20 cc) is then added and the mixture is heated under reflux for 4 hours. Assay of the solution obtained by HPLC with external calibration shows that it contains metronidazole (4.89 g) and 2-methyl-4(or 5)-nitroimidazole (0.95 g).

The degree of conversion of 1-acetoxymethyl-2-methyl-4-nitroimidazole is 81%.

The yield of metronidazole is 71.5% relative to the 1-acetoxymethyl-2-methyl-4-nitroimidazole introduced and 88% relative to the 1-acetoxymethyl-2-methyl-4-nitroimidazole converted.

EXAMPLE 3

1-Acetoxymethyl-2-methyl-4-nitroimidazole (7.96 g; 0.04 mole) and di(2-acetoxyethyl) sulphate (10.8 g; 0.04 mole) are introduced into a round-bottomed flask equipped with a magnetic stirrer. The reaction mixture is heated to 80° C. for 4 hours. Methanol (20 cc) is then added and the mixture is heated under reflux for 4 hours. After the mixture is cooled to 20° C., the pH is adjusted to 11.7 by adding concentrated sodium hydroxide (d=1.33) (5.5 cc). The precipitate which forms is separated by filtration and washed twice with methanol (3 cc).

After being dried, a product (4.61 g) is obtained in which the mixture of imidazole derivatives is composed of metronidazole (98.6%) and 2-methyl-4(or 5)-nitroimidazole (0.6%) (HPLC with internal standardization).

Analysis of the product obtained, by HPLC with external calibration, shows that it contains metronidazole (2.85 g) and 2-methyl-4(or 5)-nitroimidazole (0.014 g).

Analysis of the filtrate by HPLC with external calibration shows that it contains metronidazole (2.15 g) and 2-methyl-4(or 5)-nitroimidazole (0.93 g).

The degree of conversion of 1-acetoxymethyl-2-methyl-4-nitroimidazole is 81.4%.

The yield of metronidazole is 90% relative to the 1-acetoxymethyl-2-methyl-4-nitroimidazole converted.

EXAMPLE 4

A. Glycol diacetate (23.4 g; 0.16 mole) and concentrated sulphuric acid (d =1.83) (7.84 g; 0.08 mole) are introduced into a distillation apparatus in which the receiver is immersed in an acetone/dry ice bath.

A pressure of 15 mm Hg (2 kPa) is established, and the reaction mixture is then heated for 3 hours to 100° C., acetic acid (8 g) being distilled off.

Di(2-acetoxyethyl) sulphate is recovered in the boiling vessel in the form of a yellow oil.

B. Di(2-acetoxyethyl) sulphate (7 g), prepared above, and 1-acetoxymethyl-2-methyl-4-nitroimidazole (5.1 g; 0.026 mole) are introduced into a round-bottomed flask equipped with a magnetic stirrer. The reaction mixture is heated to 80° C. for 6 hours. Water (13 cc) is then added and heating is continued for 4 hours at 90° C.

In the solution obtained, metronidazole (2.39 g) and 2-methyl-4-(or 5)-nitroimidazole (1.03 g) are assayed by HPLC with external calibration.

The degree of conversion of 1-acetoxymethyl-2-methyl-4-nitroimidazole is 68%.

The yield of metronidazole is 54.5% relative to the 1-acetoxymethyl-2-methyl-4-nitroimidazole introduced and 79% relative to the 1-acetoxymethyl-2-methyl-4-nitroimidazole converted.

EXAMPLE 5

Di(2-acetoxyethyl) sulphate (6 g), prepared under the conditions of Example 4, and 1-acetoxymethyl-2-methyl-4-nitroimidazole (4.38 g; 0.022 mole) are introduced into a round-bottomed flask equipped with a magnetic stirrer. The reaction mixture is heated for 6 hours to 80° C., methanol (11 cc) is then added and heating is continued under reflux for 4 hours.

In the solution obtained, metronidazole (2.47 g) and 2-methyl-4(or 5)-nitroimidazole (0.82 g) are assayed by HPLC with external calibration.

The degree of conversion of 1-acetoxymethyl-2-methyl-4-nitroimidazole is 71%.

The yield of metronidazole is 65.6% relative to the 1-acetoxymethyl-2-methyl-4-nitroimidazole introduced and 93% relative to the 1-acetoxymethyl-2-methyl-4-nitroimidazole converted.

EXAMPLE 6

A. Glycol diacetate (9 g; 0.062 mole) and methanesulphonic acid (6 g; 0.062 mole) are introduced into a distillation apparatus in which the receiver is immersed in an acetone/dry ice bath. A pressure of 15 mm Hg (2 kPa) is established in the apparatus, and the reaction medium is then heated to 110° C. for 4 hours. During the heating, acetic acid (2.81 g) is distilled off.

A pale yellow oil containing acetoxyethylene glycol mesylate (80% by weight) is recovered in the boiling vessel.

The acetoxyethylene glycol mesylate is characterized by:

its infrared spectrum, in which the main characteristic absorption bands expressed in cm$^{-1}$ are 1740 (acetate C=O), 1360 (C—O) and 1180 (SO$_2$—O)

its proton nuclear magnetic resonance spectrum (360 MHz; CD$_3$CN; chemical shifts in ppm): 4.36 (t), 4.26 (t), 3.07 (s) and 2 (s).

B. Acetoxyethylene glycol mesylate (2.5 g), obtained above, and 1-acetoxymethyl-2-methyl-4-nitroimidazole (1.427 g; 0.072 mole) are introduced into a round-bottomed flask equipped with a magnetic stirrer. The reaction mixture is heated to 90° C. for 6 hours. Ethanol (20 cc) is then added and the mixture is heated under reflux for 1 hour.

Assay of the solution obtained by high performance liquid chromatography (HPLC) with external calibration shows that it contains metronidazole (0.932 g) and 2-methyl-4(or 5)-nitroimidazole (0.120 g).

The degree of conversion of 1-acetoxymethyl-2-methyl-4-nitroimidazole is 87%.

The yield of metronidazole is 77% relative to 1-acetoxymethyl-2-methyl-4-nitroimidazole introduced and 89% relative to the 1-acetoxymethyl-2-methyl-4-nitroimidazole converted.

EXAMPLE 7

Acetoxyethylene glycol mesylate (2.5 g) (obtained according to Example 6) and 1-acetoxmethyl-2-methyl-4-nitroimidazole (1.405 g; 0.0071 mole) are introduced into a round-bottomed flask equipped with a magnetic stirrer. The reaction mixture is heated to 90° C. for 6 hours. Water (20 cc) is then added and the mixture is heated to 80° C. for 1 hour.

Assay of the solution obtained by HPLC with external calibration shows that it contains metronidazole (0.907 g) and 2-methyl-4(or 5)-nitroimidazole (0.112 g).

The degree of conversion of 1-acetoxymethyl-2-methyl-4-nitroimidazole is 88%.

The yield of metronidazole is 74% relative to the 1 acetoxymethyl-2-methyl-4-nitroimidazole introduced and 85% relative to the 1-acetoxymethyl-2-methyl-4-nitroimidazole converted.

EXAMPLE 8

Di(2-acetoxyethyl) sulphate (5.4 g) and 1-acetoxymethyl-4-nitroimidazole b 1.85 g) are introduced into a round-bottomed flask equipped with a stirrer. Xylene (30 cc) is added and the mixture is then heated to 80° C for 6 hours. Water (30 cc) is then added and the reaction mixture is then heated under reflux for 4 hours.

Assay of the aqueous phase by high performance liquid chromatography (HPLC) with external calibration shows that:

the degree of conversion of 1-acetoxymethyl-4-nitroimidazole is 88% the yield of 1-hydroxyethyl-5-nitroimidazole is 97% relative to the 1 acetoxymethyl-4-nitroimidazole converted.

We claim:

1. A process for preparing a 1-hydroxyalkyl-5-nitroimidazole, which comprises: condensing a hydroxyalkylating agent of formula:

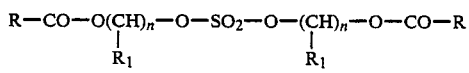

in which R denotes alkyl of 1 to 4 carbon atoms, n is 2 or 3, and the symbols R$_1$, which may be identical or different, denote hydrogen or alkyl of 1 to 4 carbon atoms, at 60 to 100° C. with an imidazole derivative of formula:

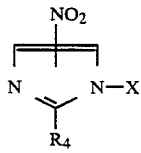

in which R$_4$ denotes hydrogen or alkyl of 1 to 4 carbon atoms, alkenyl of 2 to 4 carbon atoms, the said alkyl and alkenyl radicals being unsubstituted or substituted by one or more identical or different radicals chosen from phenyl, phenoxy, and 5- or 6-membered oxygen-containing heterocyclic radicals;

or alternatively, R$_4$ denotes aryl of 6 to 10 carbon atoms, unsubstituted or substituted by one or more identical or different substituents chosen from halogen, alkyl of 1 to 4 carbon atoms, alkoxy of 1 to 4 carbon atoms, phenyl, phenoxy, and nitro;

or alternatively, R$_4$ denotes cycloalkyl of 5 or 6 carbon atoms: the aforesaid phenyl, phenoxy, or heterocyclic radicals being unsubstituted or substituted by one or more identical or different substituents chosen from halogen, alkyl of 1 to 4 carbon atoms, alkoxy of 1 to 4 carbon atoms, phenyl, phenoxy and nitro; and X denotes hydrogen or a hydroxymethyl radical, an alkoxymethyl radical in which the alkyl portion contains 1 to 4 carbon atoms, acyloxymethyl radical in which the acyl portion contains 1 to 4 carbon atoms, an allylic ethylenic radical, or an arylmethyl radical, hydrolysing or alcoholysing the product and isolating the 1-(hydroxyalkyl)imidazole.

2. A process according to claim 1, wherein in the said hydroxyalkylating agent one of the symbols $R_1$ denotes hydrogen and the other denotes hydrogen or methyl, R is methyl and n is 2.

3. A process according to claim 1 for preparing 1-hydroxyethyl-2-methyl-5-nitroimidazole, wherein di(2-acetoxyethyl) sulphate is reacted with a said imidazole in which $R_4$ is methyl.

4. A process for preparing a 1-hydroxyalkyl-5-nitroimidazole, which comprises: reacting a product of formula:

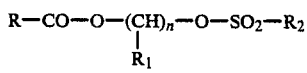

in which R denotes alkyl of 1 to 4 carbon atoms, n is 2 or 3, the symbols $R_1$, which may be identical or different, denote hydrogen or alkyl of 1 to 4 carbon atoms and $R_2$ denotes alkyl of 1 to 4 carbon atoms or an unsubstituted or substituted phenyl radical, at 60 to 100° C. with an imidazole derivative of formula:

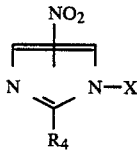

in which $R_4$ denotes hydrogen or alkyl of 1 to 4 carbon atoms, alkenyl of 2 to 4 carbon atoms, the said alkyl and alkenyl radicals being unsubstituted or substituted by one or more identical or different radicals chosen from phenyl, phenoxy, and 5- or 6-membered oxygen-containing heterocyclic radicals;

or alternatively, $R_4$ denotes aryl of 6 to 10 carbon atoms, unsubstituted or substituted by one or more identical or different substituents chosen from halogen, alkyl of 1 to 4 carbon atoms, alkoxy of 1 to 4 carbon atoms, phenyl, phenoxy, and nitro;

or alternatively, $R_4$ denotes cycloalkyl of 5 or 6 carbon atoms: the aforesaid phenyl, phenoxy, or heterocyclic radicals being unsubstituted or substituted by one or more identical or different substituents chosen from halogen, alkyl of 1 to 4 carbon atoms, alkoxy of 1 to 4 carbon atoms, phenyl, phenoxy and nitro; and X denotes hydrogen or a hydroxymethyl radical, an alkoxymethyl radical in which the alkyl portion contains 1 to 4 carbon atoms, acyloxymethyl radical in which the acyl portion contains 1 to 4 carbon atoms, an allylic ethylenic radical, or an arylmethyl radical, hydrolysing or alcoholysing the product and isolating the 1-hydroxyalkyl-5-nitroimidazole.

5. A process for preparing a 1-hydroxyalkyl-5-nitroimidazole, which comprises reacting a product of formula:

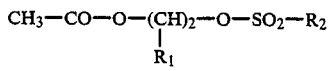

in which $R_2$ denotes methyl and one of the symbols $R_1$ denotes hydrogen and the other denotes hydrogen or methyl, with an imidazole derivative of formula:

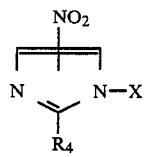

in which $R_4$ denotes hydrogen or alkyl of 1 to 4 carbon atoms, alkenyl of 2 to 4 carbon atoms, the said alkyl and alkenyl radicals being unsubstituted or substituted by one or more identical or different radicals chosen from phenyl, phenoxy, and 5- or 6-membered oxygen-containing heterocyclic radicals;

or alternatively, $R_4$ denotes aryl of 6 to 10 carbon atoms, unsubstituted or substituted by one or more identical or different substituents chosen from halogen, alkyl of 1 to 4 carbon atoms, alkoxy of 1 to 4 carbon atoms, phenyl, phenoxy, and nitro;

or alternatively, $R_4$ denotes cycloalkyl of 5 or 6 carbon atoms: the aforesaid phenyl, phenoxy, or heterocyclic radicals being unsubstituted or substituted by one or more identical or different substituents chosen from halogen, alkyl of 1 to 4 carbon atoms, alkoxy of 1 to 4 carbon atoms, phenyl, phenoxy and nitro; and X denotes hydrogen or a hydroxymethyl radical, an alkoxymethyl radical in which the alkyl portion contains 1 to 4 carbon atoms, acyloxymethyl radical in which the acyl portion contains 1 to 4 carbon atoms, an allylic ethylenic radical, or an arylmethyl radical, at a temperature of between 60° and 100° C., hydrolysing or alcoholysing the product obtained, and isolating the 1-hydroxyalkyl-5-nitroimidazole.

6. A process for preparing 1-hydroxyethyl-2-methyl-5-nitroimidazole, which comprises reacting 2-acetoxyethyl mesylate, with an imidazole derivative of formula:

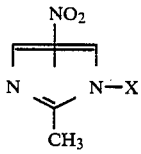

in which X denotes a hydrogen atom or a hydroxymethyl radical, an alkoxymethyl radical in which the alkyl portion contains 1 to 4 carbon atoms or acyloxymethyl radical in which the acyl portion contains 1 to 4 carbon atoms, or an allylic ethylenic radical or an arylmethyl radical, at a temperature of between 60° and 100° C., hydrolysing or alcoholysing the product obtained and isolating 1-hydroxyethyl-2-methyl-5-nitroimidazole.

7. A process according to claim 1 wherein the reaction is performed in an organic solvent chosen from esters, ethers, ketones and aromatic hydrocarbons.

8. A process according to claim 7, wherein the solvent is methyl or ethyl acetate, methyl tert-butyl ether, methyl isobutyl ketone, toluene or xylene.

* * * * *